United States Patent
Thomas et al.

(10) Patent No.: US 9,408,701 B2
(45) Date of Patent: Aug. 9, 2016

(54) REUSABLE ORTHOPAEDIC INSTRUMENT

(71) Applicants: Kyle B. Thomas, Denver, CO (US);
Thomas E. Wogoman, Warsaw, IN (US)

(72) Inventors: Kyle B. Thomas, Denver, CO (US);
Thomas E. Wogoman, Warsaw, IN (US)

(73) Assignee: DEPUY (IRELAND) (IE)

( * ) Notice: Subject to any disclaimer, the term of this patent is extended or adjusted under 35 U.S.C. 154(b) by 423 days.

(21) Appl. No.: 13/830,940

(22) Filed: Mar. 14, 2013

(65) Prior Publication Data
US 2013/0204385 A1 Aug. 8, 2013

Related U.S. Application Data (63) Continuation of application No. 13/457,752, filed on Apr. 27, 2012, which is a continuation of application No. 12/241,764, filed on Sep. 30, 2008, now Pat. No. 8,187,283.

(51) Int. Cl.
*A61F 2/38* (2006.01)
*A61F 2/46* (2006.01)
*A61F 2/30* (2006.01)

(52) U.S. Cl.
CPC .............. *A61F 2/3859* (2013.01); *A61F 2/389* (2013.01); *A61F 2/4684* (2013.01); *A61F 2/38* (2013.01); *A61F 2002/30691* (2013.01); *A61F 2002/30772* (2013.01)

(58) Field of Classification Search
CPC .......... A61F 2/3859; A61F 2/46; A61F 2/461
USPC ................. 623/20.35, 20.16, 20.31
See application file for complete search history.

(56) References Cited

U.S. PATENT DOCUMENTS

| | | | |
|---|---|---|---|
| 3,605,527 A | 9/1971 | Gambale | |
| 4,721,104 A | 1/1988 | Kaufman et al. | |
| 4,950,298 A | 8/1990 | Gustilo et al. | |
| 5,417,693 A * | 5/1995 | Sowden | A61B 17/1659 269/234 |
| 5,702,464 A | 12/1997 | Lackey et al. | |
| 5,732,992 A * | 3/1998 | Mauldin | A61F 2/461 269/134 |
| 5,755,800 A * | 5/1998 | O'Neil | A61F 2/30734 623/20.16 |
| 5,776,201 A * | 7/1998 | Colleran | A61F 2/4684 606/88 |
| 6,093,184 A | 7/2000 | Campbell et al. | |
| 6,827,739 B2 | 12/2004 | Griner et al. | |
| 8,187,283 B2 * | 5/2012 | Thomas | A61F 2/4684 606/102 |
| 8,551,179 B2 * | 10/2013 | Jones | A61F 2/3859 623/20.31 |
| 2003/0225457 A1 * | 12/2003 | Justin | A61F 2/3859 623/20.14 |
| 2004/0039450 A1 * | 2/2004 | Griner | A61B 17/155 623/20.31 |
| 2004/0153086 A1 | 8/2004 | Sanford | |
| 2004/0172137 A1 * | 9/2004 | Blaylock | A61F 2/30734 623/20.16 |
| 2004/0230197 A1 | 11/2004 | Tornier et al. | |

(Continued)

FOREIGN PATENT DOCUMENTS

| | | | |
|---|---|---|---|
| GB | 2420715 A | 7/2006 | |
| JP | 2003164460 A | 6/2003 | |

(Continued)

*Primary Examiner* — Christian Sevilla
(74) *Attorney, Agent, or Firm* — Barnes & Thornburg LLP (57) ABSTRACT

A reusable orthopedic instrument includes a reusable orthopedic trial having a first outer surface and a second outer surface that is opposite the first outer surface. A notch is formed in each side of the orthopedic instrument.

15 Claims, 9 Drawing Sheets

(56) References Cited

U.S. PATENT DOCUMENTS

| | | | |
|---|---|---|---|
| 2005/0075736 A1* | 4/2005 | Collazo | A61F 2/4684 623/20.16 |
| 2005/0124998 A1* | 6/2005 | Coon | A61F 2/3859 606/99 |
| 2007/0173946 A1 | 7/2007 | Bonutti | |
| 2007/0208349 A1 | 9/2007 | Bastian et al. | |
| 2007/0233266 A1 | 10/2007 | Williams et al. | |
| 2010/0082111 A1* | 4/2010 | Thomas | A61F 2/4684 623/20.33 |
| 2011/0218541 A1* | 9/2011 | Bailey | A61B 17/56 606/88 |
| 2012/0215319 A1* | 8/2012 | Thomas | A61F 2/4684 623/20.32 |
| 2013/0006378 A1* | 1/2013 | Wogoman | A61F 2/3859 623/20.35 |
| 2013/0116795 A1* | 5/2013 | Wogoman | A61F 2/3859 623/20.35 |

FOREIGN PATENT DOCUMENTS

| | | | | |
|---|---|---|---|---|
| WO | WO 9730661 A1 | | 8/1997 | |
| WO | WO 2008/054389 | * | 5/2008 | A61B 17/15 |

* cited by examiner

REUSABLE ORTHOPAEDIC INSTRUMENT

This patent application is a continuation of and claims priority to and the benefit of U.S. Utility patent application Ser. No. 13/457,752 entitled "REUSABLE ORTHOPAEDIC INSTRUMENT HAVING DRAIN HOLES," by Kyle Thomas, which was filed on Apr. 27, 2012, and U.S. Pat. No. 8,187,283 entitled "REUSABLE ORTHOPAEDIC INSTRUMENT HAVING DRAIN HOLES," by Kyle Thomas, which was filed on Sep. 30, 2008, the entireties of which are expressly incorporated herein by reference.

TECHNICAL FIELD

The present disclosure relates generally to reusable orthopaedic instruments, including reusable orthopaedic trials.

BACKGROUND

Various orthopaedic surgical procedures involve the use of a number of orthopaedic instruments, including orthopaedic trials, for example. For example, during a typical total knee arthroplasty (TKA) tibial trials, such as tibial trial trays and tibial trial inserts, are used to assist a surgeon in preparing the tibial surface for implantation of the tibial portion of the artificial knee. A surgeon often uses a tibial insert trial to determine the tibial implant size and to ensure a proper alignment and tibial component thickness prior to implanting the tibial components themselves, for example.

Certain types of orthopaedic instruments such as saw blades, for example, are made of metal, but others, such as trials for example are oftentimes formed from molded polymers. Many such orthopaedic instruments are cleaned and sterilized after use in a particular orthopaedic surgical procedure and then reused in subsequent surgical procedures. In a typical cleaning or sterilization process, the tools may be autoclaved. In such a process, the reusable orthopaedic tools are placed in sterilization trays for cleaning and sterilization.

SUMMARY

According to one aspect of the present disclosure, a reusable orthopaedic instrument includes a reusable orthopaedic trial having a first outer surface and a second outer surface that is opposite the first outer surface. The second outer surface includes a drainage surface that has a plurality of sidewalls extending outwardly therefrom to form a cavity. A drain hole is formed in the drainage surface at a location within the cavity such that the drain hole extends through the orthopaedic trial from the second outer surface to the first outer surface. Further, the drainage surface slopes downwardly from the plurality of sidewalls toward the drain hole.

In one illustrative embodiment, the reusable orthopaedic trial may be one of a femoral trial, a tibial trial, a tibial insert trial, a tibial augment trial, a femoral augment trial, a tibial stem trial, a femoral stem trial, a hip cup trial, a hip liner trial, a hip stem trial, a shoulder cup trial, a shoulder liner trial, a shoulder stem trial, and a trauma trial.

In another illustrative embodiment, the reusable orthopaedic trial may be made from a polymer material. Further illustratively, the reusable orthopaedic trial may be made from an injection molded polymer material.

In still another illustrative embodiment, the plurality of sidewalls may be positioned around the entire periphery of the cavity.

In yet a further illustrative embodiment, the second outer surface may include a second drainage surface including a second plurality of sidewalls extending outwardly therefrom to form a second cavity. A second drain hole may be formed in the second drainage surface at a location within the second cavity such that the second drain hole extends through the reusable orthopaedic trial from the second outer surface to the first outer surface. Illustratively, the second drainage surface may slope downwardly from the second plurality of sidewalls forming the second cavity toward the second drain hole.

According to another aspect of the present disclosure, a reusable orthopaedic instrument includes a body having a first outer surface and a second outer surface that is opposite the first outer surface. The second outer surface includes a drainage surface including a plurality of sidewalls extending outwardly therefrom to form a cavity. A drain hole is formed in the drainage surface at a location within the cavity such that the drain hole extends through the body of the orthopaedic instrument from the second outer surface to the first outer surface. The drainage surface slopes downwardly from the plurality of sidewalls toward the drain hole.

In one illustrative embodiment, the reusable orthopaedic instrument may be a reusable orthopaedic trial. Illustratively, at least a portion of the first outer surface may define an outer, bearing surface of the reusable orthopaedic trial. As such, the drain hole may be formed through the outer, bearing surface.

In another illustrative embodiment, the reusable orthopaedic instrument is one of a knee instrument, a hip instrument, a shoulder instrument, and a trauma instrument.

In still another illustrative embodiment, the body of the reusable orthopaedic instrument is made from an injection molded polymer material.

In yet another illustrative embodiment, the reusable orthopaedic instrument may be configured to be used in an orthopaedic surgical procedure, sterilized, and reused in a subsequent orthopaedic surgical procedure.

In a further illustrative embodiment, wherein the plurality of sidewalls of the body of the reusable orthopaedic instrument may be coupled to each other.

In another illustrative embodiment, the drain hole may be generally equidistant from each of the plurality of sidewalls.

In still another illustrative embodiment, the second outer surface may also include a second drainage surface including a second plurality of sidewalls extending outwardly therefrom to form a second cavity. Further, a second drain hole may be formed in the second drainage surface at a location within the second cavity. Illustratively, the second drain hole may extend through the body of the orthopaedic instrument from the second outer surface to the first outer surface. The second drainage surface may illustratively slope downwardly from the second plurality of sidewalls toward the second drain hole.

In yet another illustrative embodiment, the plurality of sidewalls may include a curved sidewall portion. Further, the plurality of sidewalls may include a plurality of interconnected curved sidewall portions positioned around the entire periphery of the drainage surface.

According to still another aspect of the present disclosure, a reusable orthopaedic device for use in an orthopaedic surgical procedure includes a reusable orthopaedic instrument having a first outer surface and a second outer surface that is opposite the first outer surface. The second outer surface includes a drainage surface that has a plurality of sidewalls extending outwardly therefrom to form a cavity. A drain hole is formed in the drainage surface at a location within the cavity such that the drain hole extends through the reusable orthopaedic instrument from the second outer surface to the first outer surface. Finally, the drainage surface slopes downwardly from the plurality of sidewalls toward the drain hole.

In one illustrative embodiment, the reusable orthopaedic instrument is one of a femoral trial, a tibial trial, a hip trial, a shoulder trial, a trauma trial, a knee instrument, a hip instrument, a shoulder instrument, and a trauma instrument.

BRIEF DESCRIPTION OF THE DRAWINGS

The detailed description particularly refers to the accompanying figures in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

Many different orthopaedic instruments are used and reused during various orthopaedic surgical procedures. What is meant herein by the term "reusable orthopaedic instrument" is a surgical tool for use by a surgeon in performing an orthopaedic surgical procedure which is sterilized and reused in subsequent orthopaedic surgical procedures. Such reusable orthopaedic instruments include numerous types of reusable orthopaedic trials. Hence, what is meant herein by the term "reusable orthopaedic trial" is a surgical trial for use by a surgeon in performing an orthopaedic surgical procedure which is sterilized and reused in subsequent surgical procedures. As such, it should be appreciated that, as used herein, the terms "reusable orthopaedic instruments" and "reusable orthopaedic trials" are distinct from orthopaedic implants that are surgically implanted in the body of the patient.

Various reusable orthopaedic surgical instruments, such as trials, are shown and described herein. Illustratively, each of these orthopaedic instruments is formed from an injection molded polymer material to define one or more cavities therein. Of course, it is within the scope of this disclosure to include orthopaedic instruments made from other suitable materials as well. Each of the orthopaedic instruments described herein is configured to be used during an orthopaedic surgical procedure, sterilized, and reused during a subsequent orthopaedic surgical procedure. As is discussed in greater detail below, each of the orthopaedic instruments described herein includes a drain hole for draining liquid therefrom.

Figure 1:
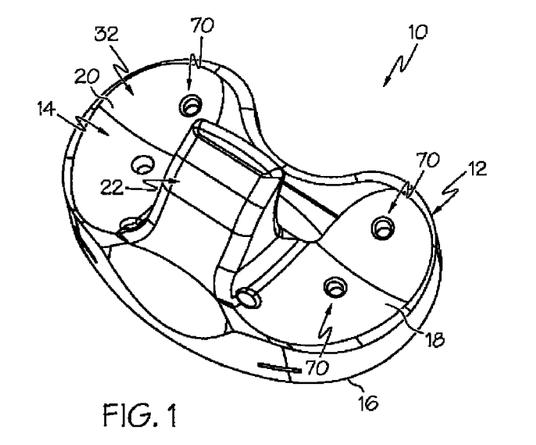
FIG. 1 is a top perspective view of an injection molded tibial insert trial having drainage holes formed therein.
Figure 2:
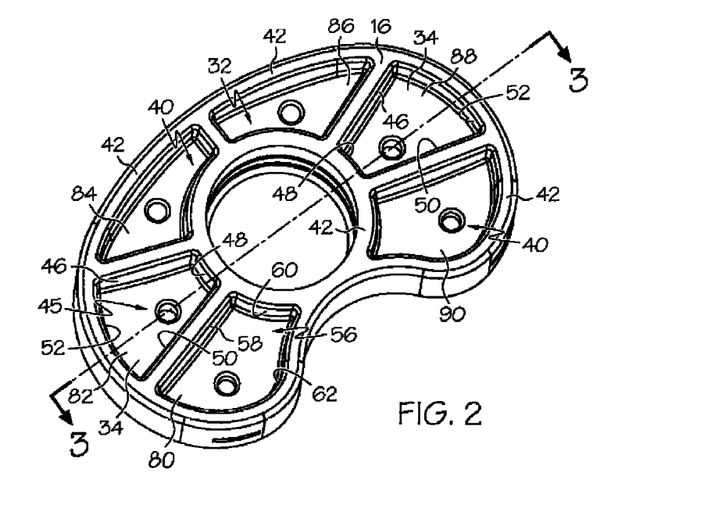
FIG. 2 is a bottom perspective view of the tibial insert trial of FIG. 2.
Figure 3:
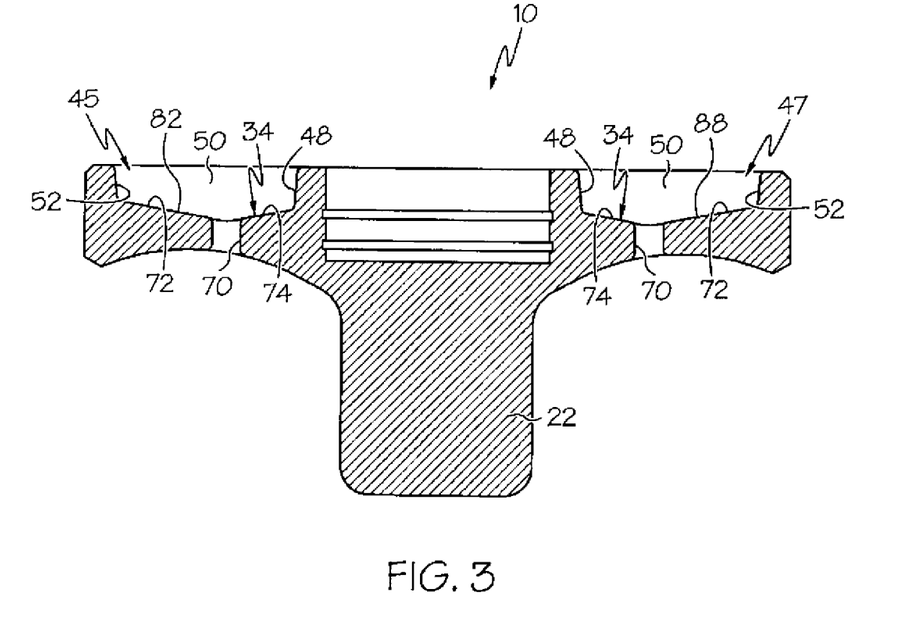
FIG. 3 is a sectional view taken along line 3-3 of FIG. 2.

Referring now to FIGS. 1-3, a reusable tibial insert trial 10 includes a platform 12 having an upper bearing surface 14 and a bottom surface 16 for placement on and engagement with a top surface of an implanted tibial trial tray (not shown), for example. In certain circumstances, the trial 10 may also be placed directly on a surface of the patient's tibia, for example. Illustratively, the trial 10 may also include other devices or features to secure the trial 10 to a tibial tray trial in a non-rotating configuration.

The upper bearing surface 14 of the trial 10 includes a medial bearing surface 18 and a lateral bearing surface 20. The medial and lateral bearing surfaces 18, 20 are configured to receive or otherwise contact corresponding medial and lateral condyles of a femoral component, such as the femoral trial 210 shown in FIGS. 4-7, for example. As such, the bearing surfaces 18, 20 may have concave contours in some embodiments. A spine 22 of the trial 10 extends upwardly from the platform 12 and is positioned between the bearing surfaces 18, 20.

Looking now to FIG. 2, the trial 10 includes an outer wall 32 defining the upper bearing surface 14 and a bone-facing interior surface 34 which is opposite the bearing surface 14. In the illustrative example of FIGS. 1-3, the bearing surface 14 and the interior surface 34 define the outer surfaces of the trial 10. As is discussed in greater detail below, the trial 10 includes a plurality of cavities 40 formed therein. Trials 10 are oftentimes molded to include such cavities in order to reduce an overall thickness of the polymer trial 10 as well as to reduce the amount of polymer used during the injection molding process. Illustratively, the trial 10 includes six cavities 40. However, it is within the scope of this disclosure to include a trial having any number of cavities formed therein. Furthermore, it is within the scope of this disclosure to include a trial having cavities of any suitable size and shape. In other words, the size and shape of the particular cavities 40 formed in the illustrative trial 10 are merely exemplary.

Illustratively, the interior surface 34 of the insert trial 10 includes a number of drainage surfaces 80, 82, 84, 86, 88, 90 having a plurality of interconnected sidewalls 42 extending outwardly therefrom. These sidewalls 42 cooperate with each other and with the drainage surfaces 80, 82, 84, 86, 88, 90 of the interior surface 34 to define the plurality of cavities 40 of the insert trial 10. In particular, each cavity 40 is defined by at least one of the drainage surfaces 80, 82, 84, 86, 88, 90 and a plurality of sidewall surfaces 44 of one or more adjacent sidewalls 42. For example, the cavities 45 and 47 are each defined by the respective drainage surface 82, 88 of the interior surface 34 as well as first, second, third, and fourth sidewall surfaces 46, 48, 50, 52. Illustratively, while the particular cavity 45 is defined by the four sidewall surfaces 46, 48, 50, 52, it is within the scope of this disclosure to include a trial 10 having a cavity formed therein that is defined by any number of sidewall surfaces extending outwardly therefrom. For example, a cavity may be defined by a single curved sidewall forming an oval or a circle. Further, a cavity may be defined by two or more curved and/or straight side walls. Illustratively, for example, the cavity 56 is defined by a first, generally straight sidewall surface 58, a second, generally curved sidewall surface 60, and a third, generally curved sidewall surface 62. Accordingly, it is within the scope of this disclosure for the tibial insert trial 10 to include a cavity defined by at least a portion of the bone-facing interior surface 34 and any number of curved and/or straight sidewall surfaces. Furthermore, the sidewalls 42 of the trial 10 are interconnected with each other and are positioned around the entire periphery of each drainage surface of the interior surface 34. It is within the scope of this disclosure, however, to include cavities defined by sidewalls which are positioned only partially around a periphery of the drainage surface.

The insert trial 10 further includes a plurality of drain holes 70, as shown in FIGS. 1 and 2. Illustratively, each drain hole 70 is formed in a respective drainage surface of the interior surface 34 (e.g., the drainage surfaces 80, 82, 84, 86, 88, 90) and extends through the outer wall 32 of the trial 10 from the interior surface 34 to the bearing surface 14 of the trial 10. In particular, each drain hole 70 is formed in one of the drainage surfaces 80, 82, 84, 86, 88, 90 at a location within one of the cavities 40. Each drain hole 70 drains any liquid collected within the cavities 40 during a cleaning and sterilization process of the insert trial 10. In other words, fluid is able to be drained from each cavity 40 through the respective drain hole 70. Illustratively, the drainage surface of each cavity 40 includes a single drain hole 70 formed therethrough. However, it is within the scope of this disclosure to provide any number of drain holes 70 within each cavity 40.

Looking now to FIG. 3, the drainage surfaces 82, 88 are shown. Illustratively, the drainage surface 82, 88 of each respective cavity 45, 47 is generally funneled in shape. In particular, the portion 72 of the drainage surface 82 between the outer sidewall surface 52 and the drain hole 70 of each cavity 45, 47 is sloped downwardly towards the drain hole 70, as shown in FIG. 3. Similarly, the portion 74 of the drainage surface 88 between the sidewall surface 48 and the drain hole 70 is also sloped downwardly towards the drain hole 70. In fact, each drainage surface is sloped downwardly towards the drain hole 70 creating a negative slope to the drain hole 70. This negative slope allows liquid to drain toward the drain hole 70 in order to maintain the sterility of the trial 10 during the cleaning and sterilization process. In other words, the drainage surfaces 80, 82, 84, 86, 88, 90 of each cavity 40 of the trial 10 slope downwardly from the plurality of sidewalls 42 defining the cavity 40 toward the drain hole 70.

While the funneled shape of the drainage surfaces 82, 88 of each cavity 45 and 47 is shown in FIG. 3 and described above, it should be understood that the drainage surface of each of the other cavities 40 of the trial 10 is also generally funneled in shape. In other words, each cavity 40 of the trial 10 includes one of the drainage surfaces 82, 84, 86, 88, 90 having downwardly sloped portions between an adjacent sidewall surface of one of the sidewalls 42 defining the cavity 40 and the drain hole.

Further illustratively, each drain hole 70 of the insert trial 10 is spaced apart from each of the sidewall surfaces of the sidewalls 42 of the cavity 40. However, as is discussed below in regards other reusable orthopaedic instruments, it is within the scope of this disclosure to position one or more of the drain holes 70 generally adjacent to one or more of the sidewall surfaces of the cavity's sidewalls 42. It is also within the scope of this disclosure to locate one or more of the drain holes 70 generally centrally within a particular cavity 40 such that the drain hole 70 is generally equidistant from each of the sidewalls 42 defining the cavity 40.

As shown in FIGS. 1-3, the tibial insert trial 10 is formed to define a plurality of cavities 40 and drainage holes 70 for draining any liquid which may collect within each cavity 40 during a cleaning and sterilization process, for example. While such structures and features are shown and described with respect to the tibial insert trial 10, it is within the scope of this disclosure to provide the same or similar drainage means in any number of orthopaedic instruments which are typically used, sterilized, and reused in subsequent orthopaedic procedures. For example, orthopaedic instruments including femoral trials such as femoral augment trials and femoral stem trials, tibial trials such as tibial tray trials, tibial stem trials, and tibial augment trials, hip trials such as hip cup trials, hip liner trials, and him stem trials, shoulder trials such as shoulder cup trials, shoulder liner trials, and shoulder stem trials, and trauma trials may each include the same or similar drainage means as that discussed above in regards to the tibial insert trial 10. Furthermore, orthopaedic instruments including knee instruments, hip instruments, shoulder instruments, and trauma instruments may also include the same or similar drainage means as that discussed above in regards to the tibial insert trial 10. Of course, other such orthopaedic instruments may include such drainage means as well. Accordingly, illustrative orthopaedic instruments including the same or similar drainage means as that disclosed above in regards to the tibial insert trial 10 of FIGS. 1-3 are shown in the remaining FIGS. 4-14 and discussed below.

Figure 4:
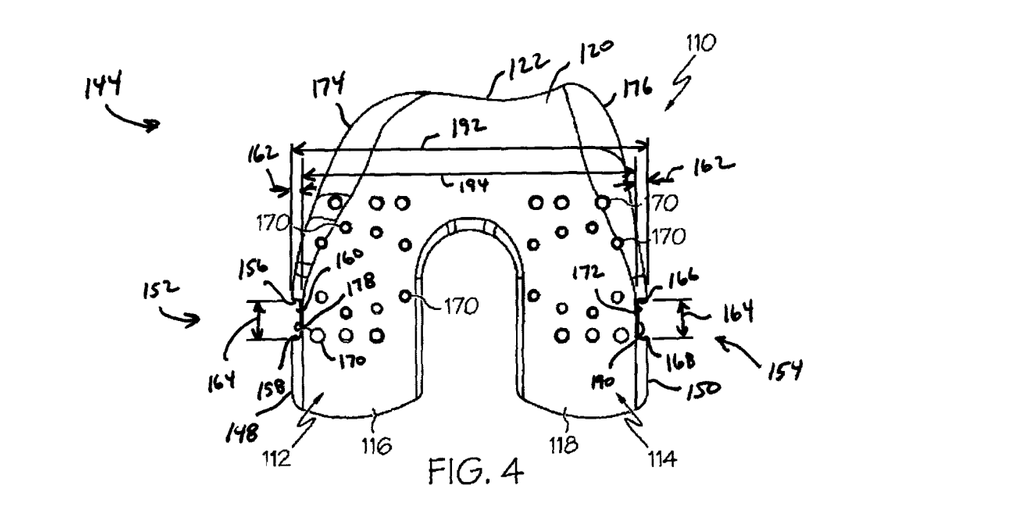
FIG. 4 is a bottom elevation view of an injection molded femoral trial having drainage holes formed therein.
Figure 5:
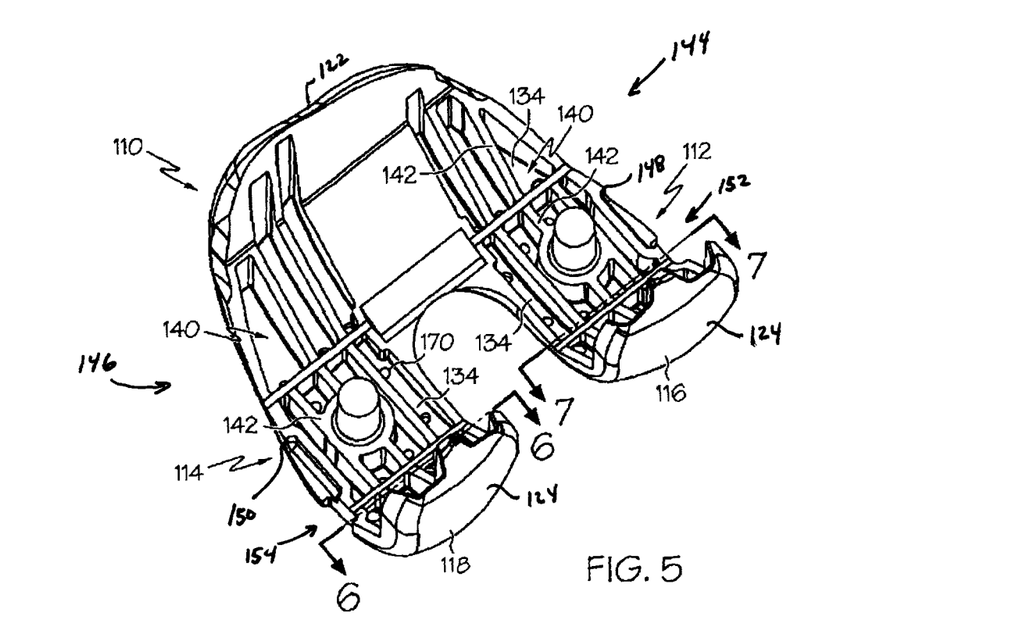
FIG. 5 is a top perspective view of the femoral trial of FIG. 4.
Figure 6:
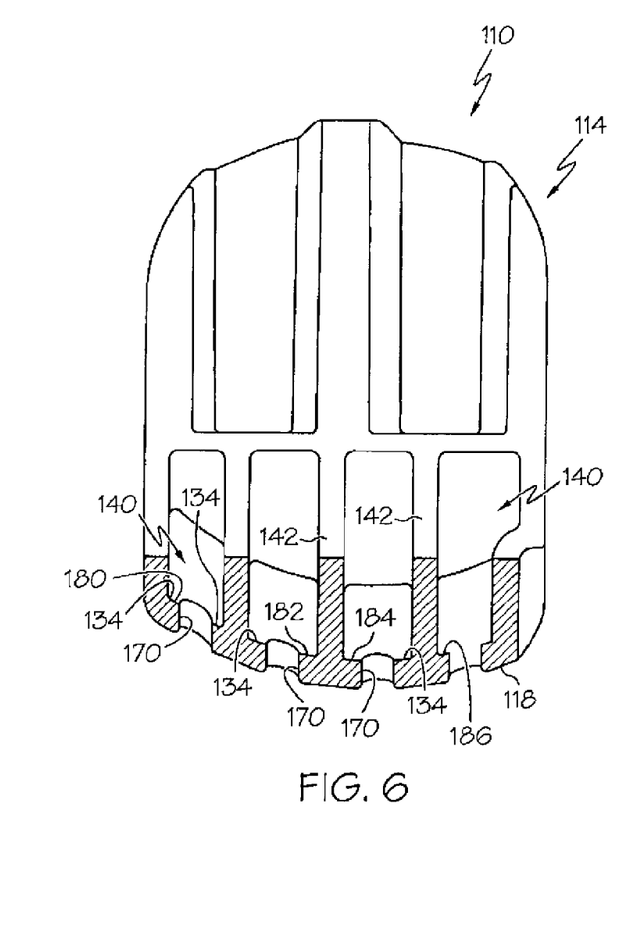
FIG. 6 is a sectional view of the femoral trial of FIGS. 4 and 5 taken along line 6-6 of FIG. 5.
Figure 7:
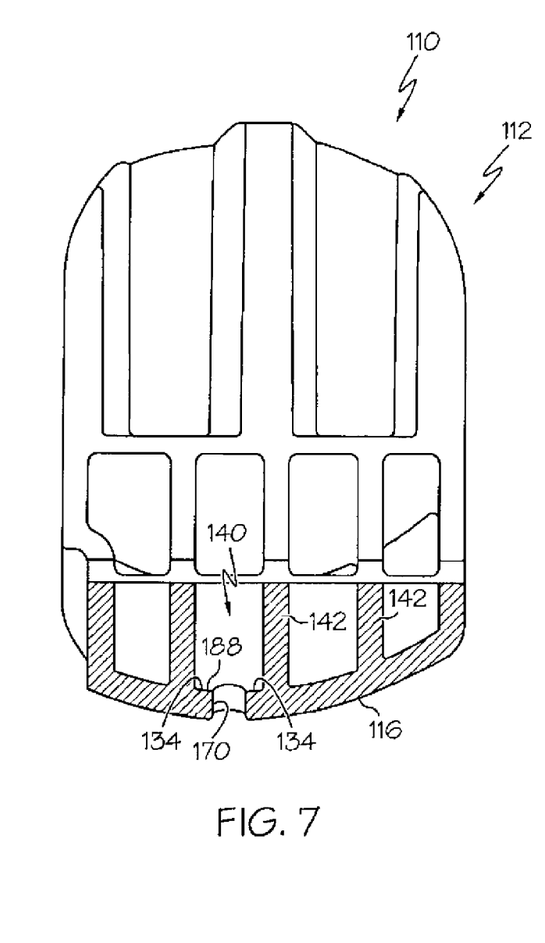
FIG. 7 is a sectional view of the femoral trial of FIGS. 4-6 taken along line 7-7 of FIG. 5.

Looking now to FIGS. 4-7, a reusable femoral trial 110 includes a pair of spaced-apart medial and lateral condyles 112, 114 defining an outer wall having an outer surface 120 including respective medial and lateral condyle surfaces 116, 118. The trial 110 also includes an anterior flange 122 and each of the medial and lateral condyles 112, 114 includes a posterior condyle 124. In use, the condyles 112, 114 are configured to articulate on corresponding bearing surfaces of a tibial insert trial, such as the trial 10 shown in FIGS. 1-3. Illustratively, the femoral trial 110 is injection molded from a polymer material and is formed to include a plurality of cavities 140. The femoral trial 110 includes a bone-facing interior surface 134 opposite the outer surface 120. In the illustrative example of FIGS. 4-7, the outer condyle surfaces 116, 118 and the bone-facing interior surface 134 define the outer surfaces of the trial 110. Illustratively, the interior surface 134 includes a plurality of drainage surfaces, such as drainage surfaces 180, 182, 184, 186, 188, as shown in FIGS. 6 and 7, for example, having a plurality of sidewalls 142 extending outwardly therefrom. The cavities 140 are defined by the various drainage surfaces and the sidewall surfaces of the sidewalls 142.

As shown in FIGS. 4-5, the medial condyle 112 is positioned on a medial side 144 of the femoral trial 110, and the lateral condyle 114 is positioned on a lateral side 146 of the femoral trial 110. A first or medial side surface 148 and a second or lateral side surface 150 extend between the outer surface 120 and the bone-facing interior surface 134 on the medial side 144 and lateral side 146, respectively. As shown in FIG. 4, the femoral trial 110 includes a pair of notches 152, 154 that are defined in the surfaces 148, 150. The notch 152 is defined by a pair of spaced-apart surfaces 156, 158 extending inwardly from the surface 144 to an inner medial surface 160. The side surfaces 156, 168 define a width 162 of the notch 152, while the inner medial surface 160 defines a length 164 that is longer than the width 162.

The other notch 154 is defined by a pair of spaced-apart surfaces 166, 168 extending inwardly from the surface 146 to an inner lateral surface 172. The side surfaces 166, 168 define a width 162 of the notch 154 extending in a medial-lateral direction, while the inner lateral surface 172 defines a length 164 extending an anterior-posterior direction, which is longer than the width 162. As shown in FIG. 4, the medial side surface 148 and the lateral side surface 150 define outer edges 174, 176, respectively, of the trial 110, while the inner medial surface 160 and the inner lateral surface 172 define outer edges 178, 190, respectively, of the trial 110. A first medial-lateral width 192 is defined between the medial side surface 148 and the lateral side surface 150, and a second medial-lateral width 194 is defined between the inner medial surface 160 and the inner lateral surface 172.

Illustratively, the femoral trial 110 further includes a plurality of drain holes 170 extending through the trial 110 from the outer condyle surfaces 116, 118 to the interior surface 134 of each respective condyle 112, 114. In particular, a drain hole 170 is formed in each drainage surface 180, 182, 184, 186, 188 that is located within each of the plurality of the cavities 140. A drain hole 170 is formed in other drainage surfaces of the trial 110 as well. Further, as shown in FIGS. 6 and 7, the respective drainage surface 180, 182, 184, 186, 188 defining each cavity 140 is sloped downwardly from the sidewall surfaces of the particular sidewalls 142 defining the cavity 140 to the drain hole 170 in order to encourage liquid to drain therethrough. Accordingly, the drainage surfaces 180, 182, 184, 186, 188 shown in FIGS. 6 and 7 as well as other drainage surfaces of the trial 110 defining each cavity 140 cooperate with the respective drain holes 170 within each cavity 140 to provide drainage means of each cavity 140 for draining liquid therefrom.

Figure 8:
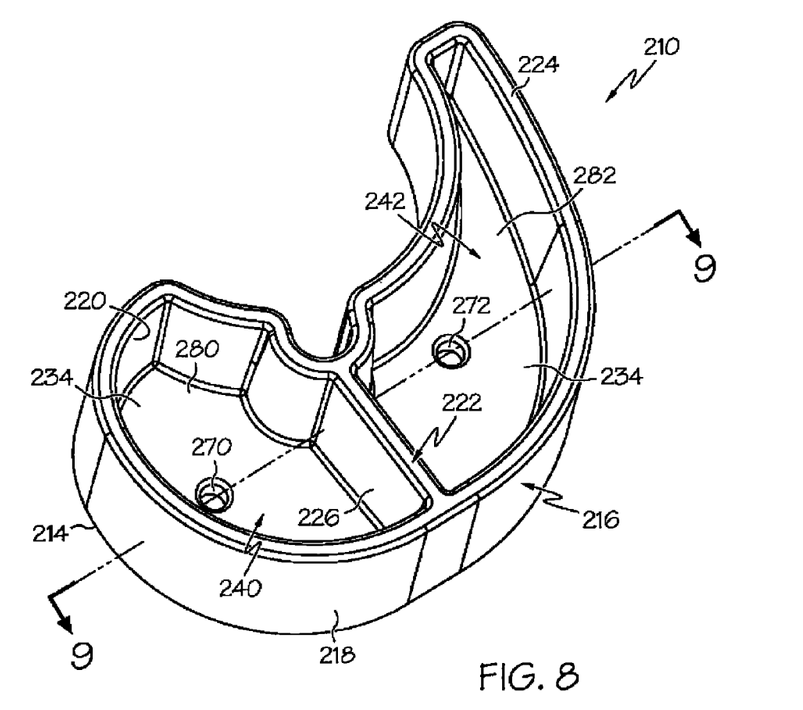
FIG. 8 is a bottom perspective view of an injection molded tibial augment trial having drainage holes formed therein.
Figure 9:
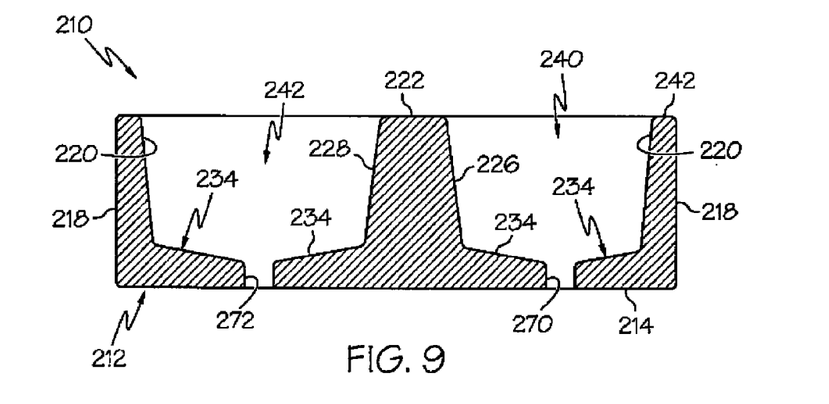
FIG. 9 is a sectional view of the tibial augment trial of FIG. 8 taken along line 9-9 of FIG. 8.

Looking now to FIGS. 8 and 9, a reusable tibial augment trial 210 includes an outer wall 212 having an outer surface 214 and an interior surface 234 which is opposite the outer surface 214. In the illustrative example of FIGS. 8 and 9, the outer surface 214 and the interior surface 234 define the outer surfaces of the trial 10. The reusable trial 210 further includes an outer sidewall 216 having an outer surface 218 and an inner surface 220. Typically, an augment trial, such as the tibial augment trial 210, is used in a revision surgery and is attached to the tibial component to account for any bone loss of the patient often seen in revision surgeries. Illustratively, the outer sidewall 216 is coupled to and extends away from the interior 234 of the outer wall 212. Further, the outer sidewall 216 is positioned about an outer perimeter of the outer wall 212. The interior surface 234 further includes a number of drainage surfaces and an inner sidewall 222 extending outwardly therefrom. In particular, the illustrative interior surface 234 of the trial 210 includes two drainage surfaces 280, 282. Illustratively, the sidewall 222 is coupled to and extends between opposed portions of the inner surface 220 of the outer wall 212 to define first and second cavities 240, 242 therein. The inner sidewall 222 includes first and second surfaces 226, 228 which cooperate with the inner sidewall surface 220 of the outer sidewall 216 to define respective first and second cavities 240, 242. Illustratively, the trial 210 further includes a bottom surface 224 of the outer sidewall 216 and the inner sidewall 222.

The reusable trial 210 further includes first and second spaced-apart drain holes 270, 272 through the outer wall 212. In particular, each drain hole 270, 272 extends between the outer surface 214 of the outer wall 212 and the respective drainage surface 280, 282 of the interior surface 234 of the outer wall 212. Further, the first drain hole 270 is formed in the first drainage surface 180 at a location within the first cavity 240 while the second drain hole 272 is formed in the second drainage surface 182 at a location within the second cavity 242. As shown in FIG. 9, the first drainage surface 280 is sloped downwardly toward the drain hole 270. In particular, portions of the first drainage surface 280 between the drain hole 270 and the inner surface 220 of the outer sidewalls 212 and the surface 226 of the inner sidewall wall 222 are sloped downwardly toward the drain hole 270 in order to encourage liquid to drain toward the drain hole 270. Similarly, portions of the second drainage surface 282 between the drain hole 272 and the inner surface 220 of the outer sidewall 212 and the surface 228 of the inner sidewall 222 of the second cavity 242 are similarly sloped downwardly away from the sidewalls 212, 222 and toward the drain hole 272. Accordingly, the first and second drainage surfaces 180, 182 and the respective drain holes 270, 272 cooperate to provide drainage means of each cavity 240, 242 for draining liquid therefrom.

Figure 10:
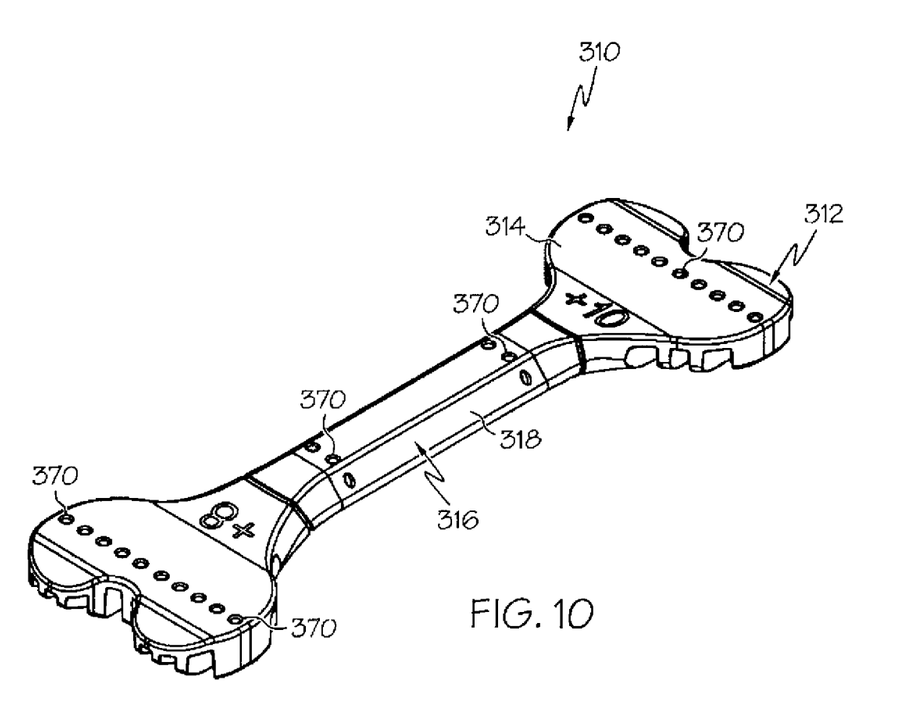
FIG. 10 is a top perspective view of an injection molded knee instrument having drainage holes formed therein.
Figure 11:
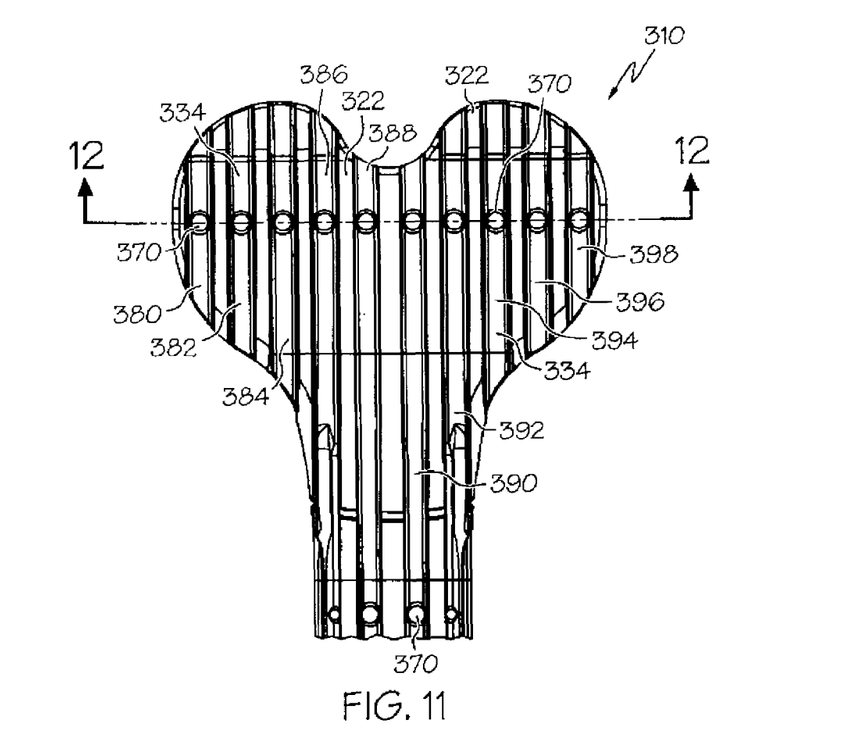
FIG. 11 is a fragmentary bottom view of the knee instrument of FIG. 10.
Figure 12:
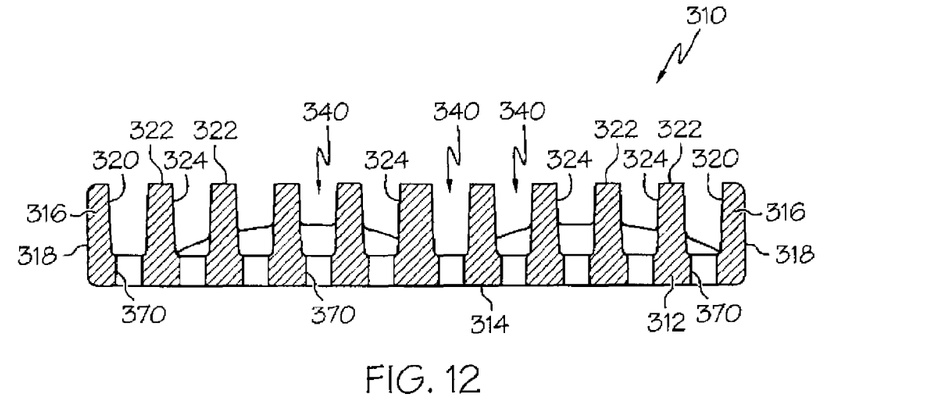
FIG. 12 is a sectional view of the knee instrument of FIGS. 10 and 11 taken along line 12-12 of FIG. 11.

Looking now at FIGS. 10-12, a reusable spacer block 310 is shown. Illustratively, the spacer block 310 includes an outer wall or body 312 having an outer surface 314 and a bone-facing interior surface 334 (shown in FIG. 11). The spacer block 310 further includes an outer sidewall 316 having an outer surface 318 and an inner surface 320 as well. In the illustrative example of FIGS. 11-12, the outer surface 314, the bone-facing interior surface 334, and the inner surface 320 define the outer surfaces of the trial 310. The interior surface 334 of the spacer block 310 includes a plurality of drainage surfaces having a plurality of sidewalls 322 extending outwardly therefrom. Illustrative drainage surfaces include drainage surfaces 380, 382, 384, 386, 388, 390, 392, 394, 396, 398, as shown in FIG. 11. The sidewalls 322 cooperate with each other and the outer sidewall 312 to define a plurality of cavities 340 of the spacer block 310. The spacer block 310 further includes a plurality of drain holes 370 through the outer sidewall 312. Each drain hole 370 is formed through the outer wall 312 at a location within one of the plurality of cavities 340.

Each drainage surface, including drainage surfaces 380-398, is sloped downwardly toward the drain hole 370 and away from the sidewalls 312, 322 defining the respective cavity 340. In particular, portions of each drainage surface of the interior surface 334 between the drain hole 370 and the sidewall surfaces 324 of the sidewalls 322 and/or the inner sidewall surface 320 of the outer sidewall 312 are sloped downwardly toward the drain hole 370 in order to encourage liquid to drain toward the drain hole 370. Accordingly, the drainage surface located within each cavity 340 and the respective drain holes 370 formed in the interior surface 334 at a location within each cavity 340 cooperate to provide drainage means of each cavity 340 for draining liquid therefrom.

Figure 13:
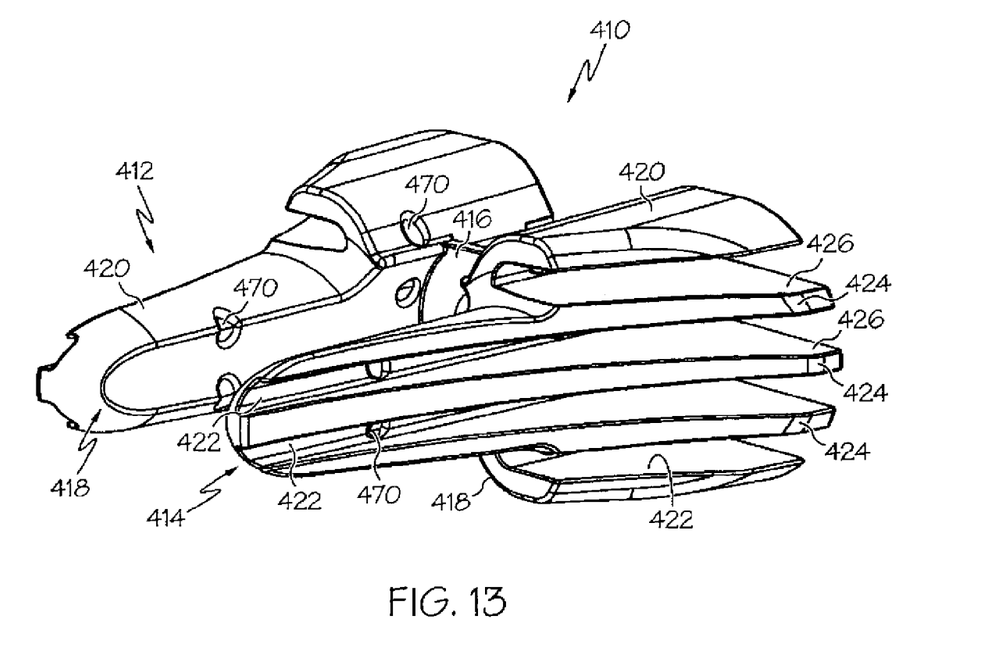
FIG. 13 is a perspective view of an injection molded impactor tip having drainage holes formed therein.
Figure 14:
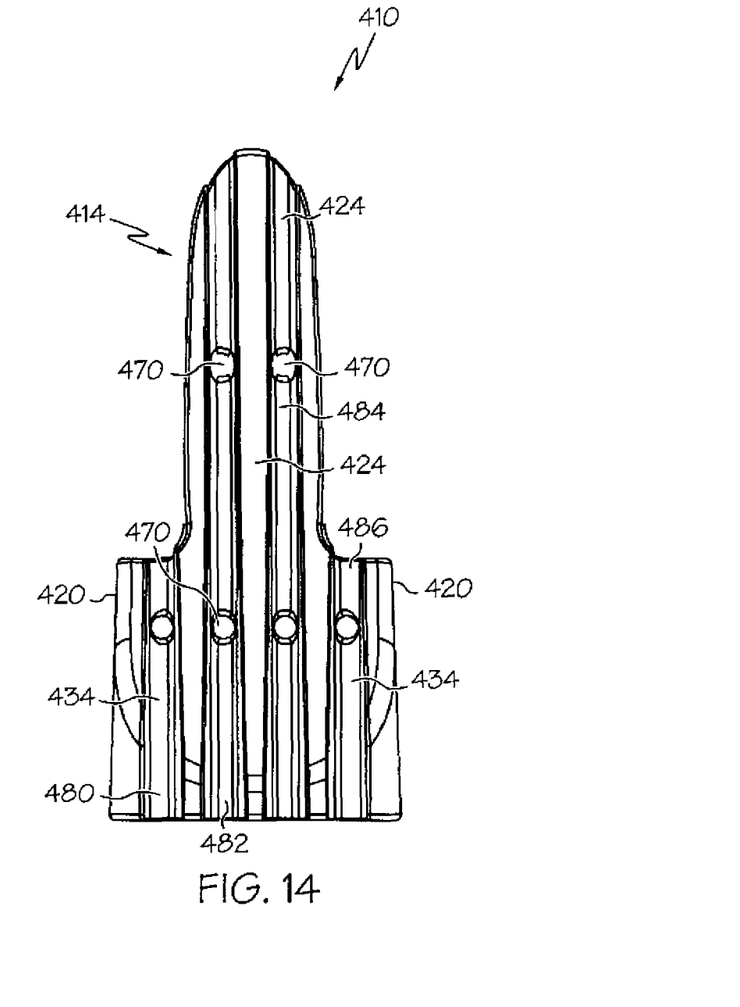
FIG. 14 is a top view of the impactor tip of FIG. 13.

Looking now to FIGS. 13 and 14, a reusable impactor 410 is shown. Illustratively, the impactor 410 includes right and left portions 412, 414 coupled to each other by a connector 416. Illustratively, each of the right and left portions 412, 414 includes an outer wall 418 having an outer surface 420 and an interior surface 422. In the illustrative example of FIGS. 13 and 14, the outer surface 420 and the interior surface 422 define the outer surfaces of the trial 410. The interior surface 422 includes a plurality of drainage surfaces having a plurality of sidewalls 424 extending outwardly therefrom. Illustrative drainage surfaces of the left portion 414 include drainage surfaces 480, 482, 484, 486, as shown in FIG. 14. Each sidewall 424 includes surfaces 426 which cooperate with each other and with the outer wall 418 to define a plurality of cavities 440 of the impactor 410. The reusable impactor 410 further includes a plurality of drain holes 470 through the outer wall 412. Each drain hole 470 is formed in one of the drainage surfaces, such as surfaces 480, 482, 484, 486 within one of the plurality of cavities 440. As shown in FIG. 14, illustrative drainage surfaces 480 and 486 each include a single drain hole 470 formed therein, whereas the drainage surfaces 482, 484 each include two drain holes 470 formed therein.

Illustratively, the drainage surfaces 480, 482, 484, 486 of each cavity 440 are each sloped downwardly away from the sidewalls 424 toward the one or more drain holes 470 located within each respective cavity 440. In particular, each drainage surface, such as surfaces 480, 482, 484, 486, located within the cavities 440 is sloped downwardly away from the inner surfaces 422 of the outer wall 418 and the sidewall surfaces 426 of the sidewalls 424 toward each drain hole 470 in order to encourage liquid to drain toward the drain holes 470. Accordingly, the drainage surfaces 480, 482, 484, 486 of each respective cavity 440 and the drain hole(s) 470 formed through the respective drainage surfaces 480, 482, 484, 486 cooperate to provide drainage means of each cavity 440 for draining liquid therefrom.

While the concepts of the present disclosure have been described in conjunction with illustrative embodiments of specific reusable orthopaedic instruments, it is within the scope of this disclosure to provide the same or similar drainage arrangements in any number of reusable orthopaedic. For example, orthopaedic instruments including femoral trials such as femoral augment trials and femoral stem trials, tibial trials such as tibial tray trials, tibial stem trials, and tibial augment trials, hip trials such as hip cup trials, hip liner trials, and him stem trials, shoulder trials such as shoulder cup trials, shoulder liner trials, and shoulder stem trials, and trauma trials may each include the same or similar drainage arrangements as that discussed above in regard to FIGS. 1-14. Other reusable orthopaedic instruments including knee instruments, hip instruments, shoulder instruments, and trial instruments may also include the same or similar drainage arrangements as that discussed above in regard to FIGS. 1-14. Of course, other reusable orthopaedic instruments may include such drainage arrangements as well.

As discussed above, each of the orthopaedic instruments 10, 110, 210, 310, 410 disclosed herein is made from an injection molded polymer material. Accordingly, the injection mold used to form the polymer includes funnel-shaped structure(s) to form the various cavities and corresponding downwardly sloped drainage surfaces located within the cavities of each of the instruments 10, 110, 210, 310, 410. Further, although the instruments 10, 110, 210, 310, 410 disclosed herein are made from a polymer material by an injection molding process, it is within the scope of this disclosure to include an orthopaedic instrument made of other suitable materials by another suitable process.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the concepts of the present disclosure arising from the various features of the systems described herein. It will be noted that alternative embodiments of each of the systems of the present disclosure may not include all of the features described yet still benefit from at least some of the advantages of such features. Those of ordinary skill in the art may readily devise their own implementations of a system that incorporate one or more of the features of the present disclosure and fall within the spirit and scope of the invention as defined by the appended claims.

The invention claimed is:

1. A reusable orthopaedic instrument comprising:
a reusable orthopaedic femoral trial including a pair of spaced apart condyles, each condyle comprising:
a first outer surface configured to articulate on a corresponding bearing surface,
a second outer surface that is opposite the first outer surface, the second outer surface being configured to be engaged with a surgically-prepared distal end of a patient's femur,
a first side surface extending between the first outer surface and the second outer surface, the first side surface defining a first outer edge of the femoral trial,
a cylindrical hole extending through the femoral trial to the first outer surface, and
a notch defined in the first side surface and extending through the first outer surface and the second outer surface of the femoral trial, the notch being defined by (i) a pair of spaced apart surfaces extending inwardly from the side surface, each spaced apart surface extending between the first outer surface and the second outer surface and (ii) a second side surface extending between the pair of spaced apart surfaces, the second side surface defining a second outer edge of the femoral trial, wherein the pair of spaced surfaces define a width of the notch extending in a medial-lateral direction and the second side surface defines a length of the notch extending in an anterior-posterior direction, the length of the notch being greater than the width of the notch.

2. The reusable orthopaedic instrument of claim 1, wherein the second side surfaces of the pair of spaced apart condyles define a first medial-lateral width.

3. The reusable orthopaedic instrument of claim 2, wherein the first side surfaces of the pair of spaced apart condyles define a second medial-lateral width greater than the first medial-lateral width.

4. The reusable orthopaedic instrument of claim 1, wherein the notches of the pair of spaced apart condyles are substantially aligned when the femoral trial is viewed in a bottom elevation view.

5. The reusable orthopaedic instrument of claim 1, wherein:
the femoral trial includes an anterior flange,
each condyle includes a posterior condyle, and
the notch of each condyle is positioned between the anterior flange and the posterior condyle.

6. The reusable orthopaedic instrument of claim 1, wherein each condyle comprises a drainage surface positioned opposite the first outer surface, wherein:
(i) the drainage surface has a plurality of sidewalls extending outwardly therefrom to form a cavity in the second outer surface,
(ii) the cylindrical hole is formed in the drainage surface at a location within the cavity, and
(iii) the drainage surface includes a section that slopes downwardly from the plurality of sidewalls toward the cylindrical hole.

7. An orthopaedic surgical instrument comprising:
a femoral trial configured to be coupled to a surgically-prepared distal end of a patient's femur, the femoral trial comprising:
an articular side comprising a medial condyle surface and a lateral condyle surface, each condyle surface having a curved contour,
a fixation side that is opposite the articular side, the fixation side comprising a fixation surface configured to engage the surgically-prepared distal end of the patient's femur,
a medial side including a first medial surface and a second medial surface that extend between the medial condyle surface and the fixation surface, and a lateral side that is opposite the medial side, the lateral side including a first lateral surface and a second lateral surface that extend between the lateral condyle surface and the fixation surface, wherein (i) the first medial surface and the first lateral surface define a first outer edge of the femoral trial and (ii) the second medial surface and the second lateral surface define a second outer edge of the femoral trial, wherein (i) a first pair of spaced surfaces extend from the first medial surface, and (ii) the second medial surface extends between and connects the first pair of spaced surfaces, the first pair of spaced surfaces and the second medial surface cooperate to define a medial notch that extends through the femoral trial component from the articular side to the fixation side, and wherein the first pair of spaced surfaces define a width of the medial notch extending in a medial-lateral direction and the second medial surface defines a length of the medial notch, the length of the medial notch being greater than the width of the medial notch.

8. The orthopaedic surgical instrument of claim 7, wherein (i) a second pair of spaced surfaces extend from the first lateral surface, and (ii) the second lateral surface extends between and connects the second pair of spaced surfaces, the second pair of spaced surfaces and the second lateral surface cooperate to define a lateral notch that extends through the femoral trial component from the articular side to the fixation side.

9. The orthopaedic surgical instrument of claim 8, wherein the medial notch is substantially aligned with the lateral notch when the femoral trial is viewed in a bottom elevation view.

10. The orthopaedic surgical instrument of claim 8, wherein the femoral trial includes:
a first medial-lateral dimension is defined between the first medial surface and the first lateral surface, and
a second medial-lateral dimension is defined between the second medial surface and the second lateral surface, the second medial-lateral dimension being greater than the first medial-lateral dimension.

11. The orthopaedic surgical instrument of claim 8, wherein the femoral trial further comprises a drainage surface positioned opposite the medial condyle surface, wherein:
the drainage surface has a plurality of sidewalls extending outwardly therefrom to form a cavity in the fixation surface,
a drain hole is formed in the drainage surface at a location within the cavity, the drain hole extending through the femoral trial to the medial condyle surface, and
the drainage surface includes a section that slopes downwardly from the plurality of sidewalls toward the drain hole.

12. The orthopaedic surgical instrument of claim 11, wherein the femoral trial further comprises a second drainage surface positioned opposite the lateral condyle surface, wherein:

the second drainage surface has a second plurality of sidewalls extending outwardly therefrom to form a second cavity in the fixation surface,
a second drain hole is formed in the second drainage surface at a location within the second cavity, the second drain hole extending through the femoral trial to the lateral condyle surface, and
the second drainage surface includes a section that slopes downwardly from the second plurality of sidewalls toward the second drain hole.

13. An orthopaedic surgical instrument, comprising:
a femoral trial configured to be coupled to a surgically-prepared distal end of a patient's femur, the femoral trial comprising (i) a medial side, (ii) a lateral side, (iii) an articular side comprising a femoral condyle surface, and (iv) a fixation side that is opposite the articular side, the fixation side being configured to engage the surgically-prepared distal end of the patient's femur, wherein:
a first notch extending from the fixation side to the articular side is defined in the medial side, the first notch comprising a pair of spaced edges extending from the medial side and a connecting edge extending between and connecting the spaced edges,
a second notch extending from the fixation side to the articular side is defined in the lateral side, the second notch comprising a pair of spaced edges extending from the medial side and a connecting edge extending between and connecting the spaced edges, and
a medial-lateral distance is defined between the connecting edge of the first notch and the connecting edge of the second notch,
wherein the first notch and the second notch are substantially aligned with each other when the femoral trial is viewed in a bottom elevation view,
wherein the femoral trial further comprises a drainage surface positioned opposite the femoral condyle surface, the drainage surface having a plurality of sidewalls extending outwardly therefrom to form a cavity in the fixation side, and a drain hole is formed in the drainage surface at a location within the cavity, the drain hole extending through the femoral condyle surface, and
wherein the drainage surface includes a section that slopes downwardly from the plurality of sidewalls toward the drain hole.

14. The orthopaedic surgical instrument of claim 13, wherein each connecting edge is longer than each spaced edge.

15. The orthopaedic surgical instrument of claim 13, wherein:
the medial-lateral distance is a first medial-lateral distance,
the medial side includes an outer medial edge,
the lateral side includes an outer lateral edge, and
a second medial-lateral distance is defined between the outer medial edge and the outer lateral edge, the second medial-lateral distance being less than the first medial-lateral distance.

* * * * *